(12) United States Patent
Roychowdhury et al.

(10) Patent No.: US 8,491,525 B2
(45) Date of Patent: Jul. 23, 2013

(54) SYSTEMS, APPARATUS AND ASSOCIATED METHODS FOR NEEDLELESS DELIVERY OF THERAPEUTIC FLUIDS

(75) Inventors: Suranjan Roychowdhury, Plymouth, MN (US); Vincent G. Copa, Minnetonka, MN (US); Sidney F. Hauschild, St. Paul, MN (US)

(73) Assignee: AMS Research Corporation, Minnetonka, MN (US)

( * ) Notice: Subject to any disclaimer, the term of this patent is extended or adjusted under 35 U.S.C. 154(b) by 386 days.

(21) Appl. No.: 11/942,080

(22) Filed: Nov. 19, 2007

(65) Prior Publication Data
US 2008/0119784 A1    May 22, 2008

Related U.S. Application Data

(60) Provisional application No. 60/866,308, filed on Nov. 17, 2006.

(51) Int. Cl.
*A61M 5/30* (2006.01)
*A61B 1/12* (2006.01)
*A61B 1/00* (2006.01)

(52) U.S. Cl.
USPC .............. 604/70; 600/156; 600/104; 600/127

(58) Field of Classification Search
USPC .............. 604/68, 70, 264; 600/104, 123, 125, 600/127, 128, 130, 154, 156
See application file for complete search history.

(56) References Cited

U.S. PATENT DOCUMENTS

| 118,206 A | 8/1871 | Crowell |
| 2,621,853 A | 12/1952 | Bollerup |
| 2,708,600 A | 5/1955 | Froidevaux |

(Continued)

FOREIGN PATENT DOCUMENTS

| WO | WO 92/04869 | 4/1992 |
| WO | WO 96/07447 | 3/1996 |

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner* — Nicholas Lucchesi
*Assistant Examiner* — Pritesh Patel
(74) *Attorney, Agent, or Firm* — Gregory L. Koeller

(57) ABSTRACT

A needleless fluid delivery system for delivering therapeutic fluids to treatment sites within a patient. The fluid delivery system can include an automated injector source and a needleless access device. The access device can include a delivery scope and a treatment specific applicator. The automated injector source, delivery scope and applicator can be operably coupled with quick-connect style fittings so as to allow for quick replacement and maintenance of used or damaged components. The automated injector source can include a hands-free input mechanism allowing a medical professional to use both hands in manipulating the delivery scope and needleless applicator at the same time an injection is desired. The delivery scope and needleless applicator can comprise flexible or rigid lengths of tubing based on the accessibility of the treatment site. The needleless delivery system can include an imaging system for precisely position the applicator with respect to the treatment location.

8 Claims, 3 Drawing Sheets

U.S. PATENT DOCUMENTS

| | | | |
|---|---|---|---|
| 2,867,375 A | 1/1959 | Petersen | |
| 3,212,684 A | 10/1965 | Svensson et al. | |
| 4,701,162 A | 10/1987 | Rosenberg | |
| 4,705,502 A | 11/1987 | Patel | |
| 4,792,330 A | 12/1988 | Lazarus | |
| 4,848,367 A | 7/1989 | Avant et al. | |
| 4,873,977 A | 10/1989 | Avant et al. | |
| 4,909,785 A | 3/1990 | Burton et al. | |
| 4,911,164 A | 3/1990 | Roth | |
| 4,932,956 A | 6/1990 | Reddy et al. | |
| 4,941,808 A | 7/1990 | Qureshi et al. | |
| 5,047,039 A | 9/1991 | Avant et al. | |
| 5,116,313 A * | 5/1992 | McGregor | 604/70 |
| 5,123,908 A | 6/1992 | Chen | |
| 5,152,772 A | 10/1992 | Sewell, Jr. | |
| 5,306,226 A | 4/1994 | Salama | |
| 5,322,418 A | 6/1994 | Comer | |
| 5,540,701 A | 7/1996 | Sharkey et al. | |
| 5,545,171 A | 8/1996 | Sharkey et al. | |
| 5,630,709 A | 5/1997 | Bar-Cohen | |
| 5,693,016 A | 12/1997 | Gumaste et al. | |
| 5,695,504 A | 12/1997 | Gifford, III et al. | |
| 5,707,380 A | 1/1998 | Hinchliffe et al. | |
| 5,833,698 A | 11/1998 | Hinchliffe et al. | |
| 5,840,062 A | 11/1998 | Gumaste et al. | |
| 5,931,842 A | 8/1999 | Goldsteen et al. | |
| 5,964,791 A | 10/1999 | Bolmsjo | |
| 6,024,748 A | 2/2000 | Manzo et al. | |
| 6,119,045 A | 9/2000 | Bolmsjo | |
| 6,149,667 A | 11/2000 | Hovland et al. | |
| 6,193,734 B1 | 2/2001 | Bolduc et al. | |
| 6,238,368 B1 | 5/2001 | Devonec | |
| 6,254,570 B1 | 7/2001 | Rutner et al. | |
| 6,299,598 B1 | 10/2001 | Bander | |
| 6,302,905 B1 | 10/2001 | Goldsteen et al. | |
| 6,391,039 B1 | 5/2002 | Nicholas et al. | |
| 6,416,545 B1 | 7/2002 | Mikus et al. | |
| 6,440,146 B2 | 8/2002 | Nicholas et al. | |
| 6,447,533 B1 | 9/2002 | Adams | |
| 6,461,367 B1 | 10/2002 | Kirsch et al. | |
| 6,485,496 B1 | 11/2002 | Suyker et al. | |
| 6,494,908 B1 | 12/2002 | Huxel et al. | |
| 6,520,974 B2 | 2/2003 | Tanner et al. | |
| 6,530,932 B1 | 3/2003 | Swayze et al. | |
| 6,562,024 B2 | 5/2003 | Alvarez de Toledo et al. | |
| 6,565,579 B2 | 5/2003 | Kirsch et al. | |
| 6,599,311 B1 | 7/2003 | Biggs et al. | |
| 6,602,243 B2 | 8/2003 | Noda | |
| 6,641,553 B1 | 11/2003 | Chee et al. | |
| 6,695,832 B2 | 2/2004 | Schon et al. | |
| 6,702,825 B2 | 3/2004 | Frazier et al. | |
| 6,719,709 B2 | 4/2004 | Whalen et al. | |
| 6,719,749 B1 | 4/2004 | Schweikert et al. | |
| 6,726,697 B2 | 4/2004 | Nicholas et al. | |
| 6,740,098 B2 | 5/2004 | Abrams et al. | |
| 6,746,456 B2 | 6/2004 | Xiao | |
| 6,746,472 B2 | 6/2004 | Frazier et al. | |
| 6,821,283 B2 | 11/2004 | Barzell et al. | |
| 2001/0049492 A1 | 12/2001 | Frazier et al. | |
| 2002/0002363 A1 | 1/2002 | Urakawa et al. | |
| 2002/0087176 A1 | 7/2002 | Greenhalgh | |
| 2003/0069629 A1 | 4/2003 | Jadhav et al. | |
| 2003/0208183 A1 | 11/2003 | Whalen et al. | |
| 2003/0229364 A1 | 12/2003 | Seiba | |
| 2004/0030320 A1 | 2/2004 | Chee et al. | |
| 2004/0078047 A1 | 4/2004 | Nicholas et al. | |
| 2004/0087995 A1 | 5/2004 | Copa et al. | |
| 2005/0070938 A1 | 3/2005 | Copa et al. | |
| 2005/0131431 A1 | 6/2005 | Copa et al. | |
| 2005/0251155 A1 | 11/2005 | Orban, III | |
| 2006/0200178 A1 | 9/2006 | Hamel et al. | |
| 2006/0264985 A1 | 11/2006 | Copa et al. | |
| 2006/0276811 A1 | 12/2006 | Copa et al. | |
| 2007/0219584 A1 | 9/2007 | Copa et al. | |
| 2008/0114203 A1 * | 5/2008 | Crank | 600/104 |
| 2009/0124974 A1 | 5/2009 | Crank et al. | |

FOREIGN PATENT DOCUMENTS

| | | |
|---|---|---|
| WO | WO 99/16359 | 4/1999 |
| WO | WO 99/21490 | 5/1999 |
| WO | WO 99/21491 | 5/1999 |
| WO | WO 99/58081 | 11/1999 |
| WO | WO 04/000135 | 12/2003 |
| WO | WO 04/000136 | 12/2003 |
| WO | WO 04/000137 | 12/2003 |
| WO | WO 04/000138 | 12/2003 |
| WO | WO 2004/034913 | 4/2004 |
| WO | 2007/013070 | 2/2007 |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

Hruby, G.W., "Comparison of a Novel Tissue Apposing Device and Standard Anastomotic Technique for Vesicourethral Anastomses," Journal of Endourology, vol. 20, Supplement 1 VP12-02, p. A69 (abstract) Aug. 2006.

Hruby, G.W., "Comparison of a Novel Tissue Apposing Device and Standard Anastomotic Technique for Vesicourethral Anastomses," Journal of Urology, vol. 175, No. 4, p. 347, Apr. 2006.

* cited by examiner

SYSTEMS, APPARATUS AND ASSOCIATED METHODS FOR NEEDLELESS DELIVERY OF THERAPEUTIC FLUIDS

PRIORITY CLAIM

The present application claims priority to U.S. Provisional Application Ser. No. 60/866,308 filed Nov. 17, 2006 and entitled, "SYSTEMS, APPARATUS, AND ASSOCIATED METHODS FOR NEEDLELESS DELIVERY OF THERAPEUTIC FLUIDS", which is herein incorporated by reference in its entirety.

FIELD OF THE INVENTION

The present invention relates generally to the delivery of therapeutic fluids as part of a healthcare treatment. More specifically, the present invention relates to a needleless system for delivering a pressurized fluid from an automated pressure source to an internal treatment site within a patient undergoing medical treatment.

BACKGROUND OF THE INVENTION

A wide variety of medical treatments are at least partially performed through the delivery and introduction of therapeutic compositions to a treatment location. In home or outpatient settings, typical delivery methods can comprise oral delivery, via liquid or solid forms, as well as a variety of inhalant style devices. In clinical or hospital settings, therapeutic fluids are commonly injected using needle based systems. In some instances, the therapeutic fluid is delivered directly into a treatment location with a shot based injection while in other instances, a needle and drip line can be used to intravenously introduce the therapeutic to the vascular system whereby the therapeutic fluid is carried and dispersed throughout the body. While needle based systems are the unquestionably preferred delivery mechanism for certain treatment methods, there remain a variety of treatment applications wherein treatment sites within the body can be accessed without the cutting or piercing access provided by a needle. As such, it would be advantageous to have a system capable of precisely delivering a therapeutic fluid to treatment sites within the body absent the cutting and/or piercing access associated with needles.

SUMMARY OF THE INVENTION

The present invention comprises a fluid delivery system and related methods for delivering therapeutic fluids to treatment sites within a patient. The fluid delivery system can comprise an automated injector source and a needleless access device. In some embodiments, the access device can comprise a delivery scope and a treatment specific applicator. In some embodiments, the automated injector source, delivery scope and applicator can be operably coupled with quick-connect style fittings so as to allow for quick replacement and maintenance of used or damaged components. In some embodiments, the automated injector source can comprise an input mechanism such as, for example, a foot pedal allowing a medical professional to provide a hands free input to the automated injector source when an injection of therapeutic fluid is desired. The delivery scope can comprise a length of flexible tube providing the medical professional an ability to easily maneuver the applicator. In some embodiments, the applicator can comprise a rigid, steerable applicator capable of being individually maneuvered directly to a treatment delivery site without the assistance of the delivery scope while in still other embodiments, the applicator can comprise a flexible tube that is passively steered by the delivery scope or in conjunction with another introduction device such as, for example, a catheter. In yet another embodiment, the fluid delivery system can comprise an imaging system allowing the medical professional to precisely position the applicator with respect to a desired treatment location.

In one aspect of the present disclosure, a needleless fluid delivery system can be used to deliver therapeutic fluids to treatment locations within a patient's body. The needleless fluid delivery system can comprise an automated injector source and an access device. In some embodiments, the access device can comprise a delivery scope and a needleless applicator. In some presently preferred embodiments, the various components of the needleless fluid delivery system can be operably, fluidly connected using quick-connect fittings allowing for quick replacement and maintenance of used or damaged components as well as providing flexibility to the needleless fluid delivery system by allowing the use of treatment specific components such as, for example, applicators that are specific to a particular type of body access or treatment location. In one representative embodiment, the automated injector source can comprise a hand-free input mechanism such as, for example, a foot pedal so as to provide a medical professional the opportunity to use both hands in properly manipulating the delivery scope and needleless applicator. Depending upon treatment location and the particular body access, the needleless applicator can be individually steerable to a treatment delivery site or the needleless applicator can be passively steered using the delivery scope or introduced with a separate introduction device such as a catheter. In yet another embodiment, the fluid delivery system can either include or be used in conjunction with an imaging system allowing the medical professional to precisely position the needleless applicator with respect, which may be especially advantageous when the automated injector source includes the hands-free input mechanism.

In another aspect of the present disclosure, a variety of applicators can be used in conjunction with a needleless fluid delivery system to deliver a therapeutic fluid to a treatment location within a patient's body. In one representative embodiment, a plurality of therapy-specific applicators can each comprise a common attachment coupling so as to be selectively, individually attachable to an automated injector source capable of operable interconnection with the attachment coupling. In some embodiments, the variety of applicators can be individually tailored to have desirable characteristics including, for example, flexibility or rigidity, steerable or non-steerable as well as a variety of treatment interfaces. Applicators can be tailored for specific treatment locations including, for example, a rectal treatment location, a gastrointestinal treatment location, a nasal treatment location, a bronchial treatment location or an esophageal treatment location. The applicator can be attachable to a delivery scope and can be configured either for placement over the delivery scope or within the delivery scope. Each applicator can comprise one or more applicator lumens for performing treatment at the treatment location. In some embodiments, a representative applicator can have an injection lumen such as, for example, an end-fire injection lumen for an end delivery of the therapeutic fluid or the applicator can have a side-fire injection lumen for a side delivery of the therapeutic fluid to the treatment location. In some embodiments, the applicator can further comprise a vacuum lumen to position and retain issue with respect to the injection lumen.

In another aspect, the present disclosure is directed to a method for delivering a therapeutic fluid to a treatment location within the body using a pressurized fluid source so as to avoid the use of a needle in accessing the treatment location. One representative method for delivering the therapeutic fluid can first comprise accessing the treatment location with an access device that includes a treatment specific applicator. In some embodiments, accessing the treatment location can include imaging the treatment location with a medical imaging system so as to verify the position of the treatment specific applicator with respect to the treatment location. Depending upon the treatment location, the treatment specific applicator can be rigid or flexible, individually steerable or carriable with an introducer, straight, curved or otherwise shaped. Presently contemplated treatments can include rectal and/or gastro intestinal, nasal, bronchial and esophageal treatments. At the treatment location, tissue to be treated can be captured and retained utilizing a vacuum introduced through the treatment specific applicator. After the treatment location has been accessed and the tissue positioned using the treatment specific applicator, the therapeutic fluid can be delivered to the treatment site under the direction of a high pressure injector. As the therapeutic fluid reaches the treatment site, the therapeutic fluid can be applied to the treatment location through an injector lumen in the treatment specific applicator.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
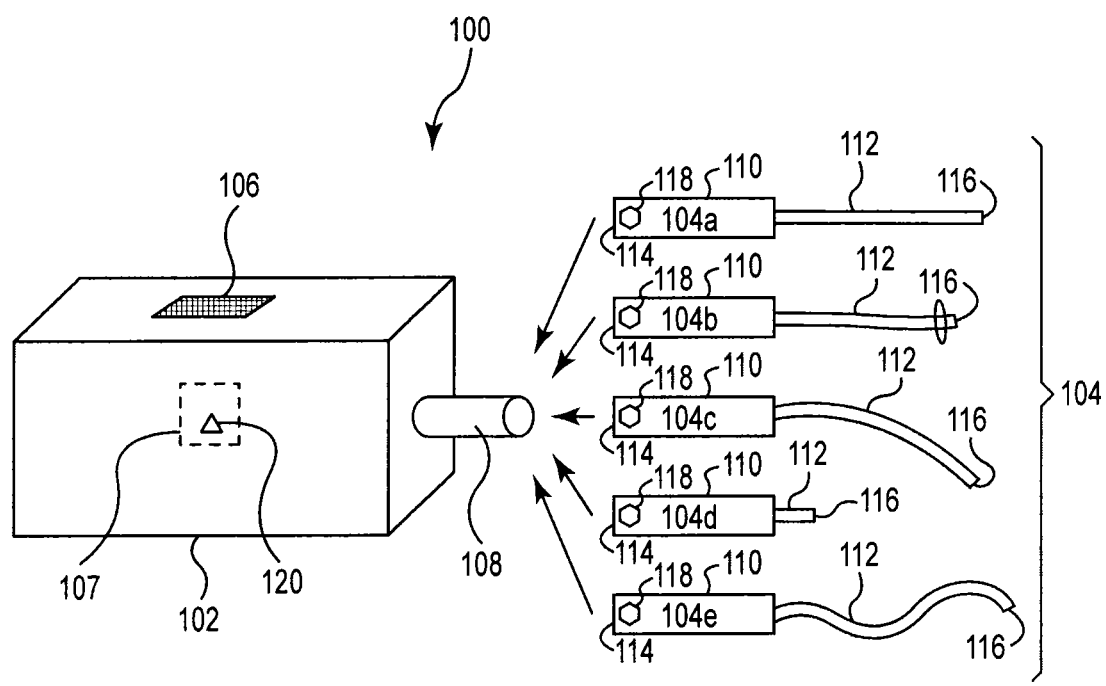
FIG. 1 is a perspective view of an embodiment of a needleless fluid delivery system for delivering a therapeutic fluid to a treatment location according to the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF THE DRAWINGS

In the following detailed description of the present invention, numerous specific details are set forth in order to provide a thorough understanding of the present invention. However, it will be obvious to one skilled in the art that the present invention may be practiced without these specific details. In other instances, well-known methods, procedures, and components have not been described in detail so as to not unnecessarily obscure aspects of the present invention.

A needleless fluid delivery system 100 is illustrated generally in FIG. 1. Needleless fluid delivery system 100 can comprise an automated injector 102 and an applicator 104. Automated injector 102 can include a user interface 106, a controller 107 and a connector member 108. User interface 106 can comprise an input means for selectively delivering a pressurized fluid through the connector member 108. Representative input means can include switches and/or buttons. In one presently preferred embodiment, user interface 106 comprise a touch-screen capable of receiving touch commands as well as displaying system information including a mode of operation as well as operating parameters. Controller 107 generally comprises a microprocessor or similar control instrument capable of communicating with user interface 106 and can include suitable memory for storing operational criteria.

As seen in FIG. 1, applicator 104 generally includes a scope portion 110 and a delivery portion 112. Generally, a delivery lumen is continuously defined from a supply end 114 on the scope portion 110 to a delivery end 116 on the delivery portion 112. Supply end 114 is generally configured to fluid attached to the connector member 108. Delivery portion 112 can comprise a variety of configurations depending upon a specified treatment location in a patient's body such as, for example, a rectal treatment location, a gastrointestinal treatment location, a nasal treatment location, a bronchial treatment location or an esophageal treatment location. In some embodiments, the delivery portion 112 can be rigid or flexible, straight or curved, long or short, and the like. Representative embodiments of applicator 104 include a male urethra applicator 104a, a prostate applicator 104b, a bladder applicator 104c, a female bladder/urethra applicator 104d or a ureter/kidney applicator 104e.

In some presently contemplated embodiments, applicator 104 and connector member 108 or controller 107 can include a mechanical or electrical communication means for automatically communicating the applicator type to the controller 107. In some embodiments, applicator 104 can comprise a microchip or a RFID tag 118 communicating with a receiving element 120 on controller 107. When applicator 104 is attached to connector member 108, RFID tag 118 can communicate and applicator type to the automated injector receiving element 120. Once the applicator type has been communicated to the receiving element 120, the controller 107 can preconfigure the automated injector 102 for standard operating conditions associated with the injector type. For example, attachment of prostate applicator 104b to connector member 108 instructs the controller 107 to prepare the automated injector 102 to prepare for standard operating conditions relative to a prostate treatment procedure.

Figure 2:
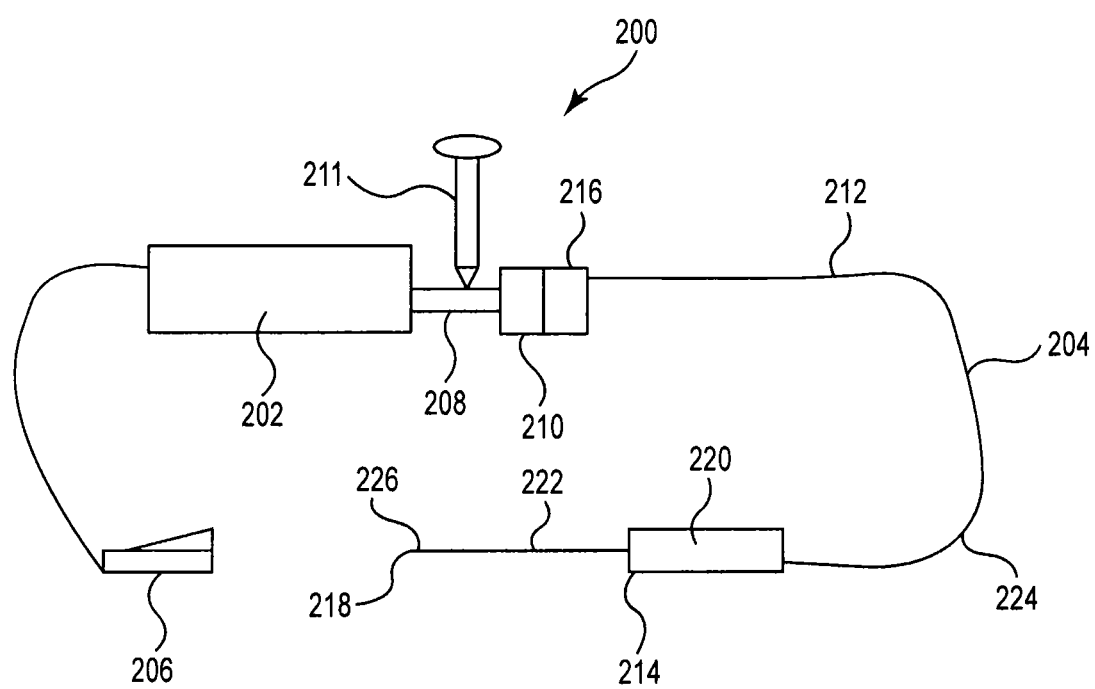
FIG. 2 is side view of an embodiment of a needleless fluid delivery system for delivering a therapeutic fluid to a treatment location according to the present disclosure.

Another representative embodiment of a needleless fluid delivery system 200 is illustrated generally in FIG. 2. Needleless fluid delivery system 200 can comprise an automated injector 202 and a treatment access device 204. Automated injector 202 can include a hands-free input device 206, a fluid reservoir 208 and an injector coupling member 210. In one presently preferred embodiment, the hands-free input device 206 can comprise a foot pedal for initiating a pressurized injection of a therapeutic fluid through the treatment access device 204. Fluid reservoir 208 can comprise a manual injector 211 for supplying the treatment fluid or to supplement the treatment fluid with additional fluid. Injector coupling member 210 preferably comprises a quick-connect style fitting and preferably comprises a swivel or rotating design for accommodating flexibility in the treatment access device 204.

Treatment access device 204 generally comprises an extension tube 212 and an applicator 214. Generally, a fluid delivery lumen is operably, continually defined from an access device coupling member 216 to a delivery end 218 of the treatment access device 204. Applicator 214 generally comprises a grasping portion 220 and a delivery portion 222. Extension tube 212 can preferably comprise a flexible extension tube 224 allowing a medical professional to manipulate the grasping portion 220 such that the delivery portion 222, and more specifically, an applicator head 226 to the desired treatment location within the body. Depending upon the treatment location, applicator 214 can also include configurations such as, for example, male urethra applicator 104a, prostate applicator 104b, bladder applicator 104c, female bladder/urethra applicator 104d or ureter/kidney applicator 104e.

Figure 3:
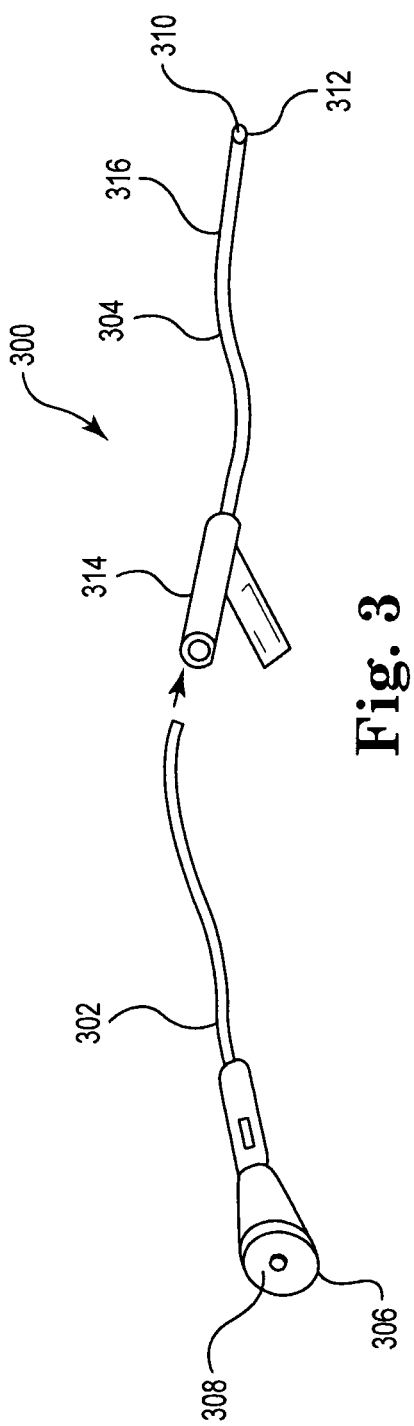
FIG. 3 is a perspective view of an embodiment of an access device for delivering a therapeutic fluid to a treatment location according to the present disclosure.

A representative embodiment of an access device 300 is illustrated in FIG. 3. Access device 300 can comprise a flexible scope 302 operably coupled to an applicator 304. Flexible scope 302 can include a supply connector 306 on a supply end 308 while applicator 304 includes an applicator head 310 proximate a delivery end 312. Supply connector 306 preferably comprises a quick-connect style fitting and can be configured for attachment to an automated injector such as, for example, automated injector 102 and/or automated injector 202. Applicator 304 generally comprises a grasping portion 314 and a delivery portion 316. Delivery portion 316 can comprise a flexible tube that is either individually steerable or passively steerable in conjunction with the flexible scope 302. Delivery portion 316 can comprise any of a variety of applicator styles dependent upon the treatment location and can include configurations such as, for example, male urethra applicator 104a, prostate applicator 104b, bladder applicator 104c, female bladder/urethra applicator 104d or ureter/kidney applicator 104e.

Figure 4B:
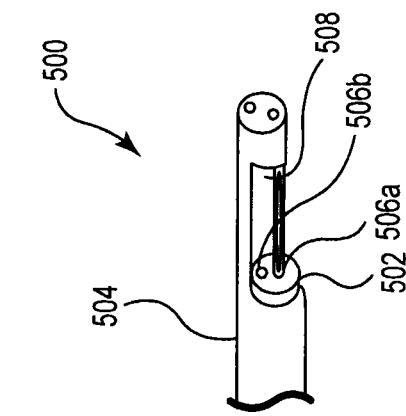
FIG. 4B is a perspective, end view of the access device of FIG. 3 in a through-scope configuration.
Figure 4A:
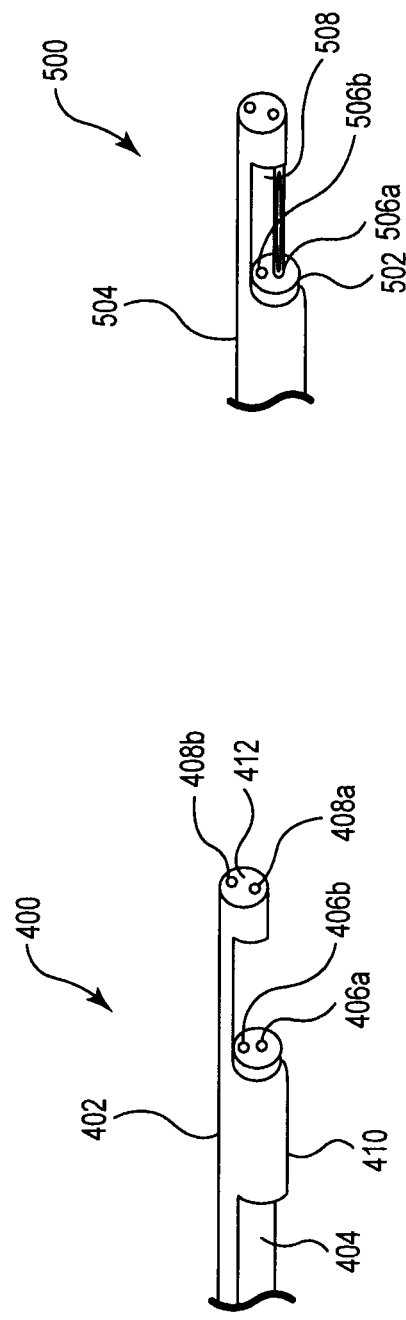
FIG. 4A is a perspective, end view of the access device of FIG. 3 in an over-scope configuration.

As illustrated in FIGS. 4A and 4B, applicator head 310 can comprise a variety of configurations depending upon convenience and efficacy in administering a therapeutic fluid at the treatment location. With reference to FIG. 4A, an over-scope applicator 400 can include a clear applicator head 402 that operably slides over a flexible scope 404. Flexible scope 404 can include a scope vacuum lumen 406a and a scope delivery lumen 406b. The flexible scope 404 can be advanced through the clear applicator head 402 until the scope vacuum lumen 406a is fluidly connected to a head vacuum lumen 408a and the scope delivery lumen 406b is fluidly connected to the head delivery lumen 408b. Applicator head 402 can include an alignment member 410 for assuring proper alignment and engagement of the applicator head 402 and the flexible scope 404. When applicator head 402 and flexible scope 404 are operably connected, an automated injector can initiate a vacuum within the scope vacuum lumen 406a and head vacuum lumen 408a such that tissue at the treatment location is drawn against a treatment end 412 of the applicator head 402. With the tissue in direct contact with the treatment end 412, an end-fire delivery of therapeutic fluid can be delivered from the automated injector, through the scope delivery lumen 406b, out the head delivery lumen 408b and onto/into the tissue.

Referring to FIG. 4B, a through-scope applicator 500 can include an applicator head 502 that operably slides through a flexible scope 504. The applicator head 502 can include an applicator vacuum lumen 506a and an applicator delivery lumen 506b. The applicator head 502 is physically configured such that the applicator vacuum lumen 506a and the applicator delivery lumen 506b are properly positioned within a working channel 508 on the flexible scope 504. When applicator head 502 is positioned proximate the working channel 508, an automated injector can initiate a vacuum within the applicator vacuum lumen 506a such that tissue at the treatment location is drawn into the working channel 508. With the tissue presented within the working channel 508, a side fire delivery of therapeutic fluid can be delivered from the automated injector, through the applicator delivery lumen 506b, and onto/into the tissue.

With respect to the various needle free therapeutic fluid delivery systems, access devices and applicators described herein, it will be understood that a medical professional preferably utilizes the systems, devices, methods and applicators as described along with a medical imaging system such as, for example, computer axial tomography (CAT), magnetic resonance imaging (MRI), or in the case of treatment of a prostate gland, the preferred imaging means is transrectal ultrasound (TRUS). Through the use of a medical imaging system, a medical professional can verify that the applicator, and more specifically, the applicator head is properly inserted and positioned with respect to the desired treatment location.

Once the applicator head is positioned with respect to the treatment location, the medical professional can initiate a vacuum using either over-scope applicator 400 or through-scope applicator 500 to position the tissue proximate the appropriate delivery lumen. After verifying that the treatment location has been positioned with respect to the delivery lumen with the medical imaging system, a user can initiate delivery of a therapeutic fluid from the automated injector. In one presently preferred embodiment, the medical professional can use both hands to properly position the applicator and initiate delivery of the therapeutic fluid with the hands-free input device 206.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

The invention claimed is:

1. A needleless fluid delivery system comprising:
    an automated injector source including a user interface, a controller having a receiving element and a connector member; and
    an applicator including a scope portion and a delivery portion, the scope portion adapted to attach to the connector member such that a pressurized fluid from the automated injector source can be delivered to a treatment site through a delivery lumen defined within the applicator, wherein the applicator includes a communication member for communicating an applicator configuration directly to the receiving element, wherein the controller preconfigures the automated injector source for standard operating conditions consistent with the applicator configuration of the applicator.

2. The needleless fluid delivery system of claim 1, wherein the user interface included an input means selected from the group consisting of: a foot pedal and a touch screen.

3. The needleless fluid delivery system of claim 1, wherein the applicator is selected from the group consisting of: a male urethra applicator, a prostate applicator, a bladder applicator, a female bladder/urethra applicator and a ureter/kidney applicator.

4. The needleless fluid delivery system of claim 1, wherein the communication member is selected from the group consisting of: a microchip and a RFID tag.

5. The needleless fluid delivery system of claim 1, wherein the scope portion includes a flexible scope and a supply connector adapted to operably attach to the connector member.

6. The needleless fluid delivery system of claim 5, wherein the delivery portion includes a flexible tube that is steerable by the flexible scope.

7. The needleless fluid delivery system of claim 6, wherein the flexible tube includes a tube vacuum lumen and a tube delivery lumen and an applicator head is slidably positioned over the flexible tube such that an applicator vacuum lumen is operably connected to the tube vacuum lumen and an applicator delivery lumen is operably connected to the tube delivery lumen wherein a vacuum source in the automated injector proximates tissue against a treatment end of the applicator head such that an injection fluid can be delivered through the applicator delivery lumen at the treatment end.

8. The needleless fluid delivery system of claim 6, wherein an applicator head is slidably advanced through the flexible tube, the applicator head including an applicator vacuum lumen and an applicator delivery lumen such that the applicator head can be advanced into a working channel in the flexible tube such that a vacuum source in the automated injector proximates tissue within the working channel wherein an injection fluid can be delivered through the applicator delivery lumen at the working channel.

\* \* \* \* \*